United States Patent [19]

Buchwald et al.

[11] Patent Number: 5,227,538
[45] Date of Patent: Jul. 13, 1993

[54] CATALYTIC ASYMMETRIC REDUCTION OF KETONES USING METAL CATALYSTS

[75] Inventors: Stephen L. Buchwald, Somerville, Mass.; Alberto Gutierrez, Rockville, Md.; Robert B. Grossman, Brookline, Mass.

[73] Assignee: Massachusetts Institute of Technology, Cambridge, Mass.

[21] Appl. No.: 792,227

[22] Filed: Nov. 14, 1991

Related U.S. Application Data

[63] Continuation-in-part of Ser. No. 698,939, May 13, 1991, abandoned, which is a continuation-in-part of Ser. No. 616,892, Nov. 21, 1990.

[51] Int. Cl.$^5$ .................. C07C 29/36; C07C 29/50
[52] U.S. Cl. .................. 568/814; 568/616; 568/698; 568/700; 568/799; 568/892; 568/939
[58] Field of Search .................. 568/700, 814, 799; 698/939; 616/892

[56] References Cited

U.S. PATENT DOCUMENTS 4,191,696 3/1980 Tourog et al. .................. 568/700

OTHER PUBLICATIONS

Nakano et al, Chem. Lett., vol. of 1988, pp. 481 to 484.
Enantioselective Synthesis with Opitcally Active Transition-Metal Catalysts (Synthesis, 1988, 645-654) Branner.
Asymmetric Hydrosilylation and Hydrocarbonylation, Ojima et al. (Asymmetric Synthesis, Chapter 4 (1984), pp. 103-146).
Asymmetric Diels-Alder Reaction by the Use of a Chiral Titanium Catalyst With Molecular Sieves 4A. Remarkable Solvent Effect on the Enantioselectivity, Narasaka, et al II (Chem. Letter. 1987, 2409-2412).
The Asymmetric Diels-Alder Reaction by the Use of a Catalytic Amount of a Chiral Titanium Reagent, Narasaka, et al. I (Chem. Lett. 1986; 1967-8).
Asymmetric Hydrogenation of B-Keto Carboxylic Esters. A Practical, Purely Chemical Access to B-Hydroxy Esters in High Enantiomeric Purity. Noyori, et al. (J. Am. Chem. Soc. 1987, 109, 5856).
Chiral and C$_2$-Symmetrical Bis(oxazolinylpyridine)fhodium(III) Complexes: Effective Catalysts for Asymmetric Hydrosilylation of Ketones, Nishiyama, et al. (Organometallics, 1989, 846-848).
Enantiomerically Pure Tertiary Alcohols by TADDOL-Assisted Additions to Ketones-or How to Make a Grignard Reagent Enantioselective, Weber et al., (Angew. Chem. Int. Ed. Engl. 1992, 31, 84-6).
Enantioselective Hydrosilylation of Acetophenone With Rhodium/Oxazolines Catalysts, Balovine, et al. (Tetrahedron Letters, 1989, 30, 5141-5144).
Asymmetric Induction Catalyzed By Conjugate Bases of Chiral Proton Acids as Ligands: Enantioselective Addition of Dialkzinc-Orthotitanate Complex to Benzaldehyde With Catalytic Ability of a Remarkable High Order, Yoshioka et al. (Tetrahedron Letters, 1989, 30, 1657-60).
Enantioselective Alkylation of Aldehyde Catalyzed by Disulfonamide-Ti(O-i-Pr)$_4$ Dialkyl Zinc System, Takahashi, et al. (Tetrahedron Letters, 1989, 30, 7095-7098).
Enantioselektive Hydrosilylierung von ketonen mit (RH(COD)Cl$_2$/Pyrdinyloxazolin Katalysatoren, Brunner et al. (Chem. Ber. 1989, 122, 499-507).

(List continued on next page.)

*Primary Examiner*—Floyd D. Higel
*Attorney, Agent, or Firm*—Thomas J. Engellenner; William C. Geary, III

[57] ABSTRACT

A process is provided for the catalytic asymmetric reduction of ketones to provide alcohol reaction products which are enriched in one enantiomer. The asymmetric reduction is accomplished utilizing an achiral metal precatalyst in combination with an optically active additive.

7 Claims, No Drawings

OTHER PUBLICATIONS

Catalytic Asymmetric Glyoxylate-Ene Reaction: A Practical Access to x-Hydroxy Esters in High Enantiomeric Pruities, Mikami, et al. (J. Am. Chem. Soc. 1990, 12, 3949-3954).

BINAP: An Efficient Chiral Element for Asymmetric Catalysis, Noyori, et al. (Acc. Chem. Res. 1990, 23, 345).

A New System For Catalytic Enantioselective Reduction of Achiral Ketones To Chiral Alcohols. Synthesis of Chiral x-Hydroxy Acids, Corey et al., (Tetrahedron Letters, 1990, 31, 611).

Beletskaya, et al., Bulletin of the Academy of Sciences of the USSR, Division of Chemical Science, vol. 3, No. 3, Part 2, (Sep. 1990), pp. 613-614.

Jung et al. Tetrahedron Letters, vol. 29, No. 48, 1988, pp. 6199-6202.

CATALYTIC ASYMMETRIC REDUCTION OF KETONES USING METAL CATALYSTS

The U.S. Government has rights in this invention pursuant to NIH Grant Number GM 34917.

RELATED APPLICATION

This application is a continuation-in-part of U.S. patent application Ser. No. 698,939, filed May 13, 1991, now abandoned, which in turn, is a continuation-in-part of U.S. patent application Ser. No. 616,892, filed Nov. 21, 1990, and entitled "Catalytic Reduction of Organic Carbonyls."

BACKGROUND OF THE INVENTION

The present invention relates to processes for catalytically reducing and/or transforming organic carbonyl compounds. More particularly, the invention relates to the catalytic asymmetric reduction of ketones.

There is often a need for optically active molecules for use as pharmaceuticals or specialty chemicals. The economy of producing such compounds can be improved where chemical synthesis yields substantially enantiomerically pure forms of such molecules. Currently known methods for the catalytic asymmetric reduction of ketone substrates utilize late transition metals (e.g., rhodium, ruthenium and iridium) with chiral ligands. Although useful, such processes are costly due to the use of expensive late transition metals and potentially hazardous reagents. Accordingly, it would be advantageous to provide safer and more economical processes for the catalytic asymmetric reduction of ketones to yield alcohols having a high level of enantiomeric purity.

It is thus an object of the invention to provide a safer and more economical process for the catalytic asymmetric reduction of ketones. Another object is to provide such a reaction where the end product of the reaction is effectively and conveniently isolated. A further object is to provide relatively safe and effective methods of catalytically reducing ketones to yield alcohol end products of high enantiomeric purity. Other objects will be apparent upon reading the disclosure which follows.

SUMMARY OF THE INVENTION

The invention provides a relatively safe and effective catalytic process for the asymmetric reduction of ketone substrates to yield alcohols having a high level of enantiomeric purity.

Unless otherwise clear from its context, the term "catalyst" is used interchangeably herein to refer both to the metal complexes or precatalysts before their activation as catalytic species, and to the active catalytic species themselves. Where an achiral "catalyst" is used in combination with an optically active additive, the complex added to the reaction mixture is referred to herein as a "catalyst", even though the actual catalytic entity may not be formed, until after activation of the complex and/or combination of the chiral additive and the complex.

Generally, the process of the invention involves first generating from a precatalyst an active species of an effective reduction catalyst which is used in the reaction. The precatalyst preferably is achiral, and it is used in combination with an optically active additive. In one embodiment, the catalyst is a titanium-containing complex, however, other catalysts may be used as well.

Activation of the precatalyst is effected by addition of a stoichiometric amount (relative to substrate) of a silane reducing reagent to the catalyst mixture. The desired organic carbonyl substrate is then allowed to react with the silane reagent in the presence of the catalyst.

The reduction of ketone substrates by this reaction yields a silicon-containing intermediate. Silicon may be cleaved from the intermediate by conventional techniques, after quenching of the catalyst, to yield a crude end product in a more reduced form than the starting compound. The end product may then be purified by known techniques.

DETAILED DESCRIPTION OF THE INVENTION

The disclosures of U.S. patent application Ser. Nos. 698,939, filed May 13, 1991, and 616,892, filed Nov. 2, 1990, are incorporated by reference herein.

The process of the invention facilitates the catalytic asymmetric reduction of ketones to alcohols having a level of enantiomeric purity. One important feature of the process of the invention is that it utilizes relatively inexpensive and safe catalysts and reducing reagents.

The basic steps of the invention involve first generating an active species of an effective catalyst which, depending upon the identity of the catalyst, may be dispensed in an organic solvent such as tetrahydrofuran, ether, toluene, benzene, hexane, or the like. Preferably, this mixture is maintained in an atmosphere of an inert gas such as argon or nitrogen within which the reduction reaction takes place. In some instances, especially where certain titanium-containing precatalysts are used as explained below in more detail, the catalyst is activated by dissolving the precatalyst in a solvent together with an alkylating or reducing agent.

Once the active catalyst is formed, approximately 0.1 to 10 mole % of catalyst is combined with about 0.1 to 100 mole % of the chiral additive in an inert solvent. The catalyst-additive mixture is then mixed with a silane reducing reagent, at about 100–300 mole %, which provides the source of hydride ion for the reduction reaction. Generally, the catalyst may be generated at room temperature. The organic carbonyl substrate is then reacted, at a temperature between about room temperature and 100° C., with the silane reagent in the presence of the optically active additive and activated catalyst. Typically, the reaction requires from about 15 minutes to 24 hours to complete. The reaction can be carried out in an inert atmosphere such as argon or nitrogen.

The reaction can be terminated by known techniques, including (in some instances) by deactivating the catalyst through the addition of aqueous sodium hydroxide.

As noted, the reduction of ketones yields a silicon-containing intermediate compound. The silicon may be cleaved from the intermediate by a variety of known extraction techniques to isolate the desired end product of the reduction reaction. For example, silicon cleavage may be effected by treatment with ethanolic or aqueous solutions of hydrochloric acid or sodium hydroxide. Subsequently, separation and drying techniques can be utilized to recover the crude product, which can then be purified by a conventional technique such as chromatography.

A variety of catalysts can be used effectively in the reduction reactions of the present invention. Exemplary catalysts broadly include those having the general formulas:

M(L)(L')(L")  (1)

M(L)(L')(L")(L''')  (2)

M(L)(L')(L")(L''')(L$^{iv}$)  (3)

M(L)(L')(L")(L''')(L$^{iv}$)(L$^v$)  (4)

where M is a group 3, 4, 5 or 6 metal, a lanthanide, or an actinide and where L, L', L", L''', L$^{iv}$ and L$^v$, independently, can be some combination of H, an alkyl group, an aryl group, a silyl group, a halogen, —OR, —SR, or —NR(R'), where R and R' may be H or an alkyl or aryl group and may be different or the same. Examples of group 3, 4, 5 or 6 metals which may be useful with the present invention include titanium, vanadium, niobium chromium, yttrium, scandium, and lanthanum. Examples of useful lanthanides include samarium, ytterbium, and lutetium. Examples of useful actinides include thorium and uranium. Titanium, however, is the most preferred metal.

Among the catalysts generally identified above, the most preferred include titanium (IV) alkoxides and titanium (IV) aryloxides, including (IV) isopropoxide, titanium (IV) ethoxide, and trichlorotitanium (IV) isopropoxide, titanium (IV) methoxide, and titanium (IV) butoxide.

Currently, the most preferred catalysts include titanium (IV) isopropoxide, titanium (IV) ethoxide and trichlorotitanium (IV) isopropoxide.

Among the particular advantages of the catalysts identified above are their properties of self-activation in the presence of a silane and their air stability. The temperature at which the catalysts should be maintained ranges from about 25° C. to 80° C. These catalysts may be useful as electronically neutral molecules, anions or cations.

The catalysts are present in the reaction in catalytic quantities, ranging from about 5-10 mole percent, relative to the substrate.

One skilled in the art will appreciate that a variety of solvents can be used with these catalysts. One general requirement of a suitable solvent is that the catalyst must be completely or partially soluble within the solvent. Complete solubility is not required as there need only be enough catalyst present in the solution to facilitate a reaction. Exemplary solvents include tetrahydrofuran, toluene, benzene, hexane, ether and the like. An additional advantage of the invention is that the substrate may be present in the organic solvent at relatively high concentrations (e.g., about 1M), thus enabling smaller reactors to be used and less waste solvent to be generated. It is noted that no solvent other than the silane itself may be required.

As noted above, the reducing reagent preferred in the present processes is a silane compound which must be capable of supplying a hydride ion during the reduction reaction. Exemplary silane compounds which may be used in these processes are represented by the formulas shown below.

R(R')SiH$_2$  (I)

RSiH$_3$  (II)

RO(R'O)SiH$_2$  (III)

$$(RO)-\underset{\underset{(OR')}{|}}{\overset{\overset{(OR'')}{|}}{Si}}-H \quad (IV)$$

$$Me_3SiO-\underset{\underset{H}{|}}{\overset{\overset{R}{|}}{Si}}-(O-\underset{\underset{H}{|}}{\overset{\overset{R}{|}}{Si}}-O)_n-\underset{\underset{H}{|}}{\overset{\overset{R}{|}}{Si}}-OSiMe_3 \quad (V)$$

where R, R' and R" represent hydride, alkyl or aryl groups and may be the same or different. Specific examples of suitable silane reducing reagents include silane, diphenylsilane, phenylsilane, diethylsilane, dimethylsilane, and triethoxysilane, trimethoxysilane and poly(methylhydrosiloxane).

Preferably, the silane reducing reagent is used in an amount ranging from about 100 to about 300% by mole as compared to the amount of the substrate.

The degree of enantiomeric excess ("ee") for the alcohol reaction product depends on a number of factors including the specific ketone being reduced and the reaction conditions. For many compounds produced through this reaction, relatively high enantiomeric excess values are obtained. In some instances the "ee" exceeds 90%.

Suitable optically active additives include amines, diamines, alcohols, diols, acids, diacids, thiols and phosphines. Exemplary compounds include (1R, 2R)-diaminocyclohexane; (1S, 2S)-diaminocyclohexane; (R)-1, 1'-Bi-2-naphthol, (S) 1, 1'-Bi-2-naphthol; (1R, 2S)-ephedrine; (1S, 2R)-ephedrine; and 1,1,4,4-tetraphenyl-2,3-O-isopropylidene-D-threitol.

The order in which the catalyst and reactants are combined is not believed to be critical. The chiral additive and silane reductant may be combined first followed by the addition of catalyst and then substrate. Also, the catalyst and silane reductant may be combined first, followed by the addition of chiral additive and then substrate. The catalyst and chiral additive may also be combined first, followed by the addition of silane reductant and then substrate.

In the above description, the mole percent is relative to the amount of substrate unless otherwise noted. Moreover, one skilled in the art will understand that inert solvents include, by way of example, tetrahydrofuran, toluene, hexane, benzene, and ether.

The invention is further illustrated by the examples which follow.

EXAMPLE 1

Asymmetric Reduction of Acetophenone to 1-phenylethanol

Titanium (IV) isopropoxide (30μL, 0.10 mmol) was added to a solution of (R,R)-1,2-bis(benzylamino)cyclohexane(29μL, 0.10 mmol) and triethoxysilane (370μL, 2.00 mmol) in THF (6 mL) under an argon atmosphere, followed by rinsing with THF (1 mL). After 30 minutes at room temperature, the mixture was heated rapidly to the reflux temperature, then allowed to cool slowly to 45° C. The mixture turned a dark bluish color. Then acetophenone (118μL, 1.01 mmol) was added. The mixture gradually decolorized, then returned to the dark color. After 16 hours the reaction mixture was quenched with 15% NaOH (4mL). The mixture was diluted with THF and water and allowed to stir vigorously. It became colorless. Five hours later, GC on a poly(phenylmethylsiloxane) column showed the mixture consisted of 96% 1-phenylethanol and 2% acetophenone (the proportion of the diamine was not determined), and GC on a chiral Cyclodex B column showed that the alcohol had an ee of 8% in favor of the (S) enantiomer. The reaction mixture was diluted with ether, and the organic layer was washed with a mixture of 1 N HCl and brine, dried over $MgSO_4$, evaporated, and dried in vacuo to give 1-phenylethanol, pure by $^1H$ NMR, in 73% yield.

EXAMPLE 2

Asymmetric Reduction of Acetophenone to 1-phenylethanol

A mixture of titanium (IV) isopropoxide (15μL, 0.05 mmol) and triethoxysilane (650 μL, 3.50 mmol) in THF (6 mL) was warmed to 46° C. Then (R,R)-1,2-bis(benzylamino)cyclohexane (300μL, 1.03 mmol) was added. A small amount of bubbling occurred. After 12 minutes acetophenone (118 μL, 1.01 mmol) was added, and the bubbling ceased. The reaction mixture turned yellow over a period of hours. After 24 hours reaction time, the mixture was quenched as described in Example 1. GC of the reaction mixture showed that all the acetophenone had been consumed, and GC on a chiral column showed that the product, 1-phenylethanol, had an ee of 37% in favor of the (S) enantiomer.

EXAMPLE 3

Asymmetric Reduction of Acetophenone to 1-phenylethanol

A mixture of titanium (IV) isopropoxide (90μL, 0.3 mmol) and 1,1,4,4-tetraphenyl-2,3-O-Isopropylidene-D-threitol (280 mg, 0.06 mmol) in THF (5 mL) under an argon atmosphere was warmed to 45° C. Then triethoxysilane (1.1 mL, 6 mmol) was added dropwise. The solution bubbled profusely. After 90 minutes the bubbling had subsided and acetophenone (350 μL, 3 mmol) was added. After 24 hours the reaction was quenched by adding THF (5 mL) and 1 N NaOH (15 mL) and allowed to stir for one hour. The mixture was then diluted with water and ether (75 ml each) and shaken vigorously. GC on a poly(phenylmethylsiloxane) column showed the compound was greater than 99% 1-phenylethanol, and GC on a chiral Cyclodex B column showed that the alcohol had an ee of 33.6% in favor of the (S) enantiomer. The ether layer was collected and dried over $MgSO_4$ to afford a milky liquid composed of a mixture of 1-phenylethanol and 1,1,4,4-tetraphenyl-2,3-O-Isopropylidene-D-threitol. This was diluted with pentane, filtered and evaporated to obtain 1-phenylethanol in 62% yield.

With respect to the above examples, it is noted that the reactions were run under an atmosphere of either nitrogen or argon. Further, the tetrahydrofuran used in the examples was distilled under argon from sodium/benzophenone ketyl before use. Ketone substrates were available from commercial sources and were sometimes purified by passage through a small column of alumina I.

The above examples are intended to be illustrative of the invention and should not be read to limit the invention to the specific reduction reactions provided in the examples. One skilled in the art will readily appreciate that the invention is applicable to the asymmetric catalytic reduction of a variety of ketone substrates.

What is claimed is:

1. A process for the catalytic asymmetric reduction of ketones, comprising the steps of:

providing a mixture of (i) a catalytic amount of an active species of a catalyst selected from the group consisting of a $M(L)(L')(L'')$, $M(L)(L')(L'')(L''')$, $M(L)(L')(L'')(L''')(L^{iv})$, and $M(L)(L')(L'')(L''')(L^{iv})(L^v)$, where M is a group 3, 4, 5 or 6 metal, a lanthanide or an actinide, and L, L', L'', L''', $L^{iv}$, $L^v$, independently, are some combination of H, an alkyl, an aryl, a silyl, a halogen, —OR, —SR, or —NR(R'), where R and R' are H, an alkyl or aryl and are different or the same, (ii) a stoichiometric amount of a silane compound able to supply a hydride ion during the reduction reaction, and (iii) a chiral additive selected from the group consisting of amines, diamines, alcohols, diols, organic acids, organic diacids, thiols, and phosphines;

reacting a ketone substrate in the presence of the mixture; and recovering and purifying an alcohol reaction product enriched in one enantiomer.

2. The process of claim 1 wherein the catalyst is selected from the group consisting of metal alkoxides and metal aryloxides.

3. The process of claim 2 wherein the catalyst is selected from the group consisting of titanium (IV) isopropoxide, trichlorotitanium (IV) isopropoxide, titanium (IV) ethoxide, titanium (IV) methoxide, and titanium (IV) butoxide.

4. The process of claim 1 wherein the silane compound is selected from the group consisting of silane, diphenylsilane, phenylsilane, diethylsilane, dimethylsilane and triethoxysilane, trimethoxysilane and poly(methylhydrosiloxane).

5. The process of claim 1 wherein the catalyst is present in an amount ranging between about 2.5 and 10 percent by mole, relative to the amount of substrate.

6. The process of claim 1 wherein the amount of chiral additive is present in an amount ranging between about 0.1 to 100 mole %, relative to the amount of substrate.

7. The process of claim 6 wherein the chiral additive is selected from the group consisting of (1R, 2R)-diaminocyclohexane; (1S, 2S)-diaminocyclohexane; (R)-1,1'-Bi-2-naphthol, (S)-1,1'-Bi-2-naphthol; (1R,2S)-ephedrine; (1S,2R)-ephedrine; and 1,1,4,4-tetraphenyl-2,3-O-isopropylidene-D-threitol.

* * * * *